United States Patent [19]
Eisner

[11] Patent Number: 4,777,574
[45] Date of Patent: Oct. 11, 1988

[54] DENTAL LAMP SHIELD OR PROPHYLACTIC

[76] Inventor: Mark R. Eisner, 3130 Turner St., Allentown, Pa. 18104

[21] Appl. No.: 111,186

[22] Filed: Oct. 22, 1987

[51] Int. Cl.⁴ .......................................... F21L 15/12
[52] U.S. Cl. .................................. 362/399; 362/804; 74/558.5
[58] Field of Search ............... 362/109, 399, 400, 804; 33/29; 16/110 R, 111 R, 114 R, 116 R, DIG. 12, DIG 18; 74/558.5; 128/132 R; 118/504, 505

[56] References Cited

U.S. PATENT DOCUMENTS

| | | | |
|---|---|---|---|
| 4,288,844 | 9/1981 | Fisher et al. | 362/33 |
| 4,517,632 | 5/1985 | Roos | 362/389 |
| 4,559,671 | 12/1985 | Andrews et al. | 362/804 X |
| 4,621,735 | 11/1986 | Coon et al. | 206/438 |
| 4,643,172 | 2/1987 | Taff et al. | 128/16 |
| 4,722,296 | 2/1988 | Bowskill et al. | 118/504 |

Primary Examiner—Stephen F. Husar
Attorney, Agent, or Firm—Sanford J. Piltch

[57] ABSTRACT

A dental lamp adjusting means protective covering, shield or prophylactic comprised of a thin, tear-resistant, semi-rigid but elastic material which is sterile and disposable for covering the entirety of each of several different types of dental lamp adjusting means providing a covering which will significantly reduce and/or prevent the spread of disease through the continued touching of the dental lamp adjusting means by non-sterile gloved or ungloved hands of dental practitioners and others.

14 Claims, 2 Drawing Sheets

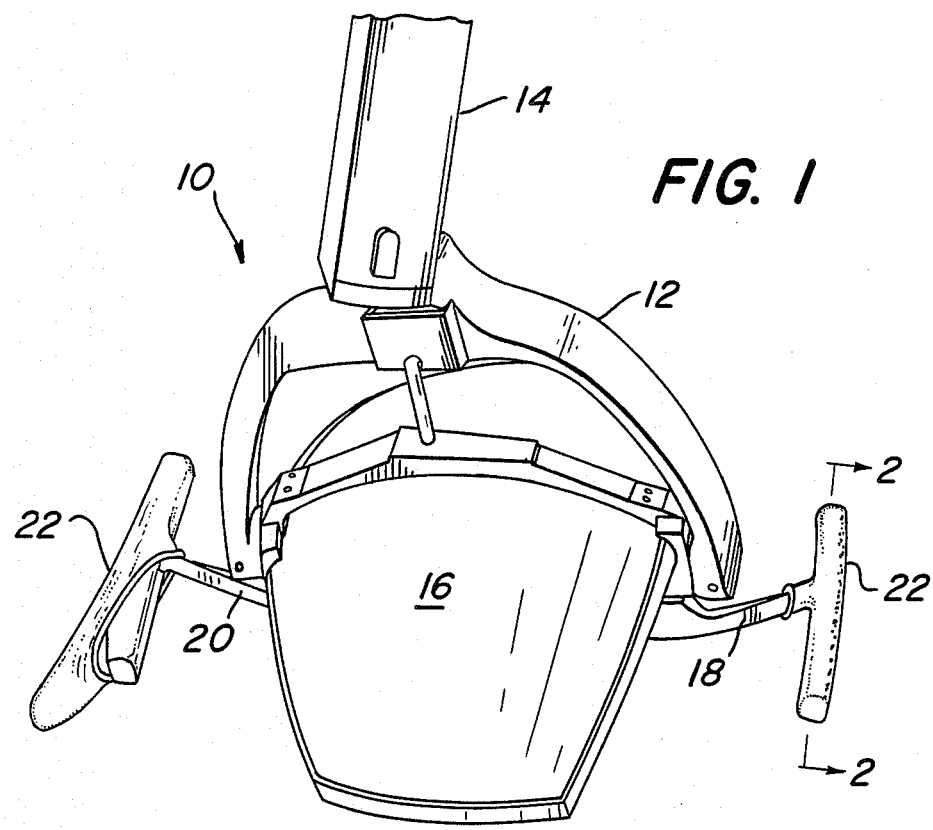
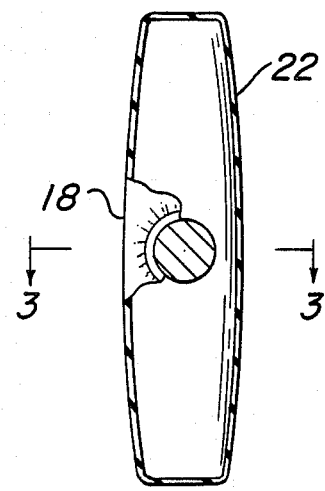
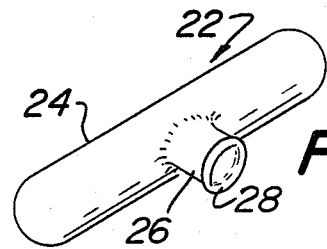
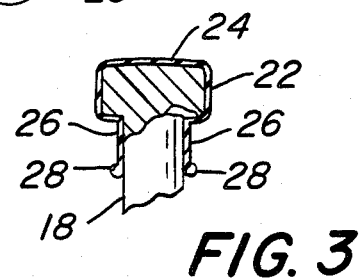

4,777,574

DENTAL LAMP SHIELD OR PROPHYLACTIC

BACKGROUND OF THE INVENTION

Dental practitioners have been aware for years that the repeated touching of the dental lamp by gloved or ungloved hands after the dental practitioner's, or the hygienist's hands have been in or around the mouths of several different patients without sterilization can bring about the spread of contagious diseases. Such contagious or communicable diseases are borne in or on the body fluids and/or tissues which become attached to the exterior surfaces of the gloved or ungloved hands of the dental practitioner or hygienist and are transmitted to the lamp handles or adjusting means through contact. More recently the spread of the Hepatitus virus and the Acquired Immune Deficiency virus have caused great concern for dental practitioners, hygienists and other dental office staff, not only for their patients, but also for their own health and well-being.

Both the Hepatitus virus and the Acquired Immune Deficiency virus are carried in or on body fluids and/or tissues. In the environment in which dental practitioners and hygienists work, i.e. inside the mouth, body fluids such as saliva, blood, etc. and the tissues comprising the gum and portions of the teeth, the pulp and root, may potentially transmit the virus through contact. The process of cleaning and/or repairing teeth by filling caries or performing a root canal procedure requires the drilling of the teeth and the subsequent scattering of tissue particles and body fluids about the mouth. Some of those particles and/or fluids become attached or adhere to the gloved or ungloved hand of the dental practitioner or hygienist. Cleaning and sterilizing the lamp handles or adjusting means between patients has been a serious problem for dental practitioners and hygienists because of their construction.

During dental procedures ranging from filling caries to cleaning teeth, the lamp is almost continually repositioned for better lighting in the interior of a patient's mouth. The lamp handles or other adjusting means are touched by the dental practitioner or hygienist in attempts to refocus the light onto the desired point interior to the patient's mouth. Refocusing the light emitted by the lamp is accomplished without the dental practitioner or hygienist sterilizing their gloved or ungloved hands while working on a patient. Anything they may have come into contact with while their hands were in the patients's mouth will be transmitted to the surface of the lamp handle or other adjusting means upon contact.

There have been some reported attempts to provide covers for surgical lamps for use in an hospital operatory. U.S. Pat. Nos. 4,559,671 [Andrews] and 4,621,735 [Coon] appear to address the problem in the almost completely sterile environment of an hospital operating room. However, little has been done to improve the level of sterilization for lamps used in the dental operatory.

The dental lamp is not thought of as a disease transmission device. It is usually cleaned, but not sterilized. The sterilization of a dental lamp, which is large and cumbersome to manipulate when not mounted to the ceiling or the wall and is not easily placed in a sterilization chamber as may be small dental instruments, is extremely difficult. The lamp may be sprayed with a disinfecting agent but such practice does not reduce or eliminate bacteria or virus forms on the lamp and usually does not occur more than possibly once or twice a day. Thus, disinfecting of the lamp does not occur between patients and certainly does not occur between hand contact with the lamp by the dental practitioner, hygienist or other staff members during the performing of dental procedures on a patient.

In recent years dental practitioners and hygienists have become increasingly aware of the rapid spread of communicable diseases through body fluids and tissues such as may be dislodged and/or become attached to the gloved or ungloved hands of the dental practitioner or hygienist during procedures in the mouth of a patient. In fact, dental practitioners, along with the dental hygienists, have been cautioned to protect themselves from infection by using sterile gloves and masks and to use protective glasses when practicing dentistry or other dental procedures on their patients. Very recently the rapid spread of the Hepatitus virus and the Acquired Immune Deficiency virus has caused significant concern among dental practitioners and hygienists. The American Dental Association and other professional organizations have strongly urged that dental practitioners and hygienists take additional steps to decrease the chance of spreading the disease through the use of non-sterile implements.

It is therefore an object of the present invention to provide a sterile protective covering or shield for the dental lamp handles or adjusting means to significantly reduce or prevent the spread of contagious, communicable diseases.

It is a further object of the present invention to provide such a shield which is disposable after a single use and which is easily applied and removed so that it will have wide-spread acceptance in the dental professions.

It is another object of the present invention to provide such a shield which is highly elastic and stretchable, yet tear resistant, and which is capable of covering the entirety of a variety of different shaped dental lamp handles.

Other objects will appear hereinafter.

SUMMARY OF THE INVENTION

The dental lamp handle or adjusting means covering, shield or prophylactic of the present invention is comprised of a thin, tear-resistant, semi-rigid but elastic material which is sterile and disposable for covering the exposed surfaces of each of several different types of dental lamp handles or adjusting means.

The present invention is an apparatus for significantly reducing or preventing the spread of communicable diseases which may be transmitted by or through contact with human body fluids and tissues during dental procedures. The apparatus comprises a removable, disposable, sterile dental lamp shield or prophylactic for placement over and in proximate contact with a dental lamp handle or adjusting means. The shield is used to significantly reduce the spread of communicable diseases during a first and subsequent uses of the dental lamp handle or adjusting means in conjunction with the treatment of two or more patients eliminating the need for repeated sterilization of said dental lamp handle and its adjusting means between such uses for two or more patients.

The shield or prophylactic is comprised of a pocket portion for fitting over the dental lamp adjusting means and a collar portion for maintaining the shield in position on said adjusting means. The pocket portion of a first embodiment is substantially cylindrical in shape having closed or sealed ends with the collar portion perpendicularly extending outward from a point substantially midway along the cylindrical portion of the shield. A second embodiment of the shield is comprised of a pocket portion which is substantially hemispheric in shape having rounded ends and a single aperture or opening with said collar portion substantially surrounding said aperture or opening. The collar portions of both embodiments have rims providing a semi-rigid opening for maintaining the sterile integrity of the shield about the opening. Additionally, aseptic medicaments or talc may be applied to the internal surface of the shield to continue disinfection and to provide a means of lubricating the shield for ease in application and removal.

The shield or prophylactic of the present invention may also be constructed to exhibit a medium to high degree of frictional contact on its outer surface.

BRIEF DESCRIPTION OF THE DRAWINGS

For the purpose of illustrating the invention, there are shown in the drawings forms which are presently preferred; it being understood, however, that the invention is not limited to the precise arrangement and instrumentalities shown.

FIG. 1 is an isometric view of a dental lamp having two handles or adjusting means showing a first embodiment of the shield or prophylactic of the present invention partially and fully applied to the handles or adjusting means, respectively.

FIG. 2 is a sectional view of the dental lamp shield or prophylactic of the present invention taken along line 2—2 of FIG. 1.

FIG. 3 is a sectional view of the dental lamp shield or prophylactic of the present invention taken along line 3—3 of FIG. 2.

FIG. 4 is an isometric view of the first embodiment of the dental lamp shield or prophylactic of the present invention.

DETAILED DESCRIPTION OF THE INVENTION

Figure 5:
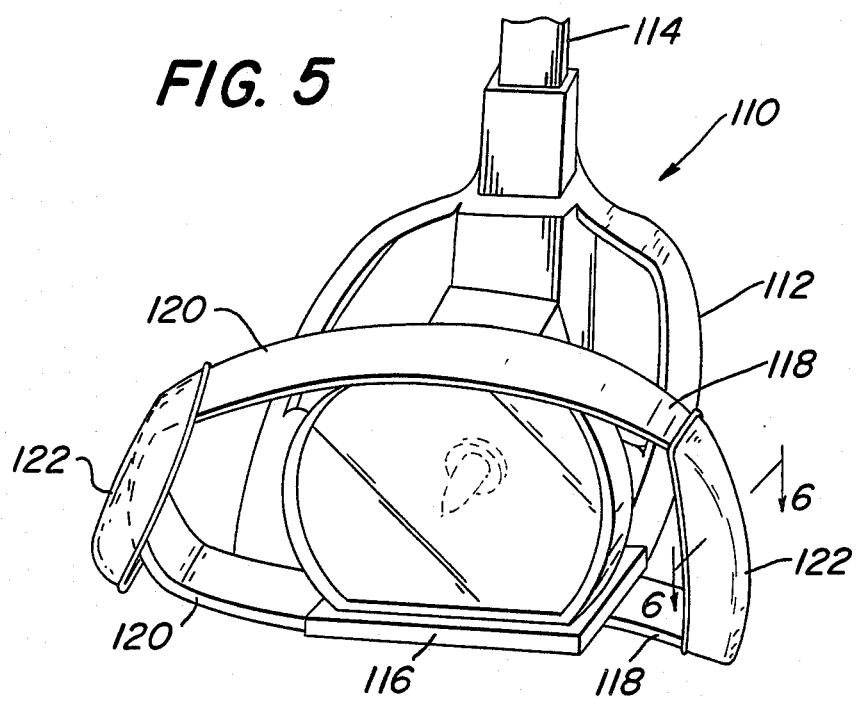
FIG. 5 is an isometric view of a dental lamp having two handles or adjusting means showing a second embodiment of the shield or prophylactic of the present invention partially and fully applied to the handles or adjusting means, respectively.

The following detailed description is of the best presently contemplated modes of carrying out the present invention. This description is not intended in a limiting sense, but is made solely for the purpose of illustrating the general principles of the invention.

Referring now to the drawings in detail, wherein like numerals represent like elements, there is shown in FIG. 1 a dental lamp 10. The dental lamp is supported from a wall or ceiling by a mounting bracket 12 having a support arm 14 as part thereof. The lamp housing 16 is attached to the mounting bracket 12 at the opposing ends of the C-shaped mounting bracket with swivel connectors. The lamp mechanism contained within the lamp housing 16 consists of the usual elements including a lamp socket with a reflecting means disposed about the socket and a lens means enclosing the front of the lamp housing. On either side of the lamp housing 16 depicted in FIG. 1 are handles or adjusting means 18, 20. The handles or adjusting means 18, 20 are T-shaped and are fixedly connected to the lamp housing 16 at a point at or near the swivel connections to the bracket 12. The handles or adjusting means 18, 20 are used to manipulate the point of focus of the lamp 10 by turning the lamp housing 16 within the swivel connectors or rotating the bracket 12 at its junction with the support arm 14.

The handles or adjusting means 18, 20 are manipulated by the dental practitioner, dental hygienist, or other member of the staff to illuminate a particular point or points in the facial area of a patient, particularly within the patient's mouth in and around the teeth and gum areas. The dental practitioner will usually make adjustments to the point of focus of the lamp 10 while examining or working within a patient's mouth. It is usual to readjust the lamp 10 several times during an examination or dental procedure, especially if the examination or procedure is lengthy. The readjustment is accomplished by grasping one or the other of the handles or adjusting means 18, 20. If the gloved or ungloved hand of the dental practitioner or other member of the staff had contacted infected tissue or body fluid, or just plain bacteria normally found within the mouth of a human and then contacted the handles to refocus the lamp, the handles or adjusting means 18, 20 have become non-sterile by such contact. The chance of passing such bacteria, or virus form, to another patient during a subsequent treatment of such patient without complete sterilization of the lamp handles or adjusting means 18, 20 is significant and highly probable.

A first embodiment of the shield or prophylactic 22 of the present invention may be applied to the dental lamp handle or adjusting means 18, 20 by sliding the shield 22 over one end of the T-shaped handle or adjusting means and stretching the shield 22 over the other end of the handle or adjusting means. A shield 22 is shown partially applied to handle or adjusting means 20 in FIG. 1. The shield 22 is shown being stretched over the second end of the T-shaped handle or adjusting means 20. Once stretched over the handle or adjusting means 18, 20, the shield 22 retracts or returns to its original shape and size about the support shaft of the handle or adjusting means 18, 20 to maintain the shield 22 in position until removal.

With reference to FIG. 4, the first embodiment of the shield 22 has an elongated cylindrical pocket portion 24 for fitting over the horizontal bar of the T-shaped handle or adjusting means 18, 20 of the lamp 10. The pocket portion 24 is required to have closed or sealed ends to fit tightly over the T-shaped handle or adjusting means 18, 20. Extending perpendicularly outward from substantially midway along the cylindrical portion of the shield 22 is a collar portion 26. The collar portion 26 extends along the handle or adjusting means 18, 20 support or control arm for a nominal distance terminating in a rim at its distal end. The rim provides a semi-rigid aperture or opening with a greater elastic memory for maintaining the sterile integrity of the shield.

The shield 22 may be formed from an elastomeric or elastic material, natural or man-made or any combination thereof. The elastomeric or elastic material should exhibit sufficient deformability to stretch over the dental lamp handle or adjusting means 18, 20, sufficient toughness and/or tear-resistance to withstand pulling and stretching during application and/or removal and sufficient material memory to return to and/or retain its original size and shape after application and/or removal. The outer surface of the shield 22 is preferred to have a medium to high degree of frictional contact to provide sufficient firmness of grasp during dental procedures where hands, gloved or ungloved, may be wet or damp from body fluids or otherwise.

Referring now to FIG. 2 and FIG. 3, the first embodiment of the shield 22 is comprised of a pocket portion which conforms to the shape of, and completely covers the T-shaped handle or adjusting means 18. The collar 26 of the shield 22 after being stretched over the ends of the T-shaped handle returns to its original size and conforms approximately to the shape of the support or control shaft of the handle or adjusting means 18. The rim 28 of the shield 22 also returns to its original size and provides a semi rigid terminus about the support or control shaft of the handle or adjusting means 18 having a greater elastic memory for maintaining a snug fit and the sterile integrity of the shield. Thus, the sterile condition of the dental lamp 10 can be maintained through the timely application and removal of the shield 22.

Referring now to FIG. 5 a second embodiment of the present invention, a dental lamp 110, is shown. The dental lamp 110 is supported from a wall or ceiling by a mounting bracket 112 having a support arm 114 as part thereof. The lamp housing 116 is attached to the mounting bracket 112 at the opposing ends of the C-shaped mounting bracket with swivel connectors. The lamp mechanism contained within the lamp housing 116 consists of the usual elements including a lamp socket with a reflecting means disposed about the socket and a lens means enclosing the front of the lamp housing. On either side of the lamp housing 116 depicted in FIG. 5 are handles or adjusting means 118, 120. The handles or adjusting means 118, 120 are C-shaped and are fixedly connected to the lamp housing 116. The handles or adjusting means 118, 120 are used to manipulate the point of focus of the lamp 110 by rotating the lamp housing 116 about the swivel junction with the support arm 114. The lamp 110 has pivotable support arms for positioning the lamp at the desired location (elevation) and a swivel junction to rotate the lamp housing 116 in the desired direction for focal point illumination.

As with the first embodiment, the second embodiment has handles or adjusting means 118, 120 which can be manipulated by the dental practitioner, dental hygienist, or other member of the staff to illuminate a particular point or points in the facial area of a patient, particularly within the patient's mouth in and around the teeth and gum areas. The dental practitioner will usually make adjustments to the point of focus of the lamp 110 while examining or working within a patient's mouth. It is usual to readjust the lamp 110 several times during an examination or dental procedure, especially if the examination or procedure is lengthy. The readjustment is accomplished by grasping one or the other of the handles or adjusting means 118, 120. If the gloved or ungloved hand of the dental practitioner or other member of the staff had contacted infected tissue or body fluid, or just plain bacteria normally found within the mouth of a human and then contacted the handles to refocus the lamp, the handles or adjusting means 118, 120 have become non-sterile by such contact. The chance of passing such bacteria, or virus form, to another patient during a subsequent treatment of such patient without complete sterilization of the lamp 110 is significant and highly probable.

The second embodiment of the shield or prophylactic 22 of the present invention may be applied to the dental lamp handle or adjusting means 118, 120 by sliding the shield 122 over one end of the C-shaped handle or adjusting means and stretching the shield 122 over the other end of the handle or adjusting means. A shield 122 is shown partially applied to handle or adjusting means 120 in FIG. 5. The shield 122 is shown being stretched over the second end of the C-shaped handle or adjusting means 120. Once stretched over the handle or adjusting means 118, 120, the shield 122 retracts or returns to its original shape and size about the support shaft of the handle or adjusting means 118, 120 to maintain the shield 122 in position until removal.

Figure 7:
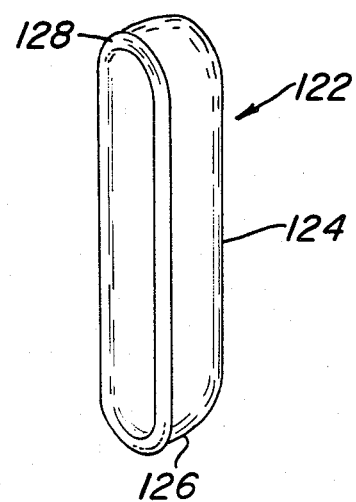
FIG. 7 is an isometric view of the second embodiment of the dental lamp shield or prophylactic of the present invention.

With reference to FIG. 7, the second embodiment of the shield 122 has an elongated hemisperical pocket portion 124 for fitting over the C-shaped handle or adjusting means 118, 120 of the lamp 110. The pocket portion 124 is required to have rounded ends to fit tightly over the C-shaped handle or adjusting means 118, 120. The pocket portion 124 of the shield 122 has a single aperture or opening. Surrounding this aperture or opening is a collar portion 126. The collar portion 126 extends along the handle or adjusting means 118, 120 support or control arm for a nominal distance creating suspended membranes on both sides of the handle or adjusting means 118, 120 and terminating in a rim 128 at its distal end. The rim 128 provides a semi-rigid terminus for the shield 122 having a greater elastic memory for maintaining a snug fit on the handle or adjusting means 118, 120 and the sterile integrity of the shield.

The shield 122 may also be formed from an elastomeric or elastic material, natural or man-made or any combination thereof. The elastomeric or elastic material should exhibit sufficient deformability to stretch over the dental lamp handle or adjusting means 118, 120, sufficient toughness and/or tear-resistance to withstand pulling and stretching during application and/or removal and sufficient material memory to return to and/or retain its original size and shape after application and/or removal. The outer surface of the shield 122 is preferred to have a medium to high degree of frictional contact to provide sufficient firmness of grasp during dental procedures where hands, gloved or ungloved, may be wet or damp from body fluids or otherwise.

Figure 6:
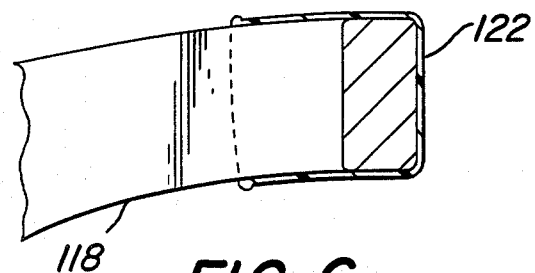
FIG. 6 is a sectional view of the dental lamp shield or prophylactic of the present invention taken along line 6—6 of FIG. 5.

Referring now to FIG. 6, the second embodiment of the shield 122 is also comprised of a pocket portion 124 and a collar portion 126 which conform to the shape of, and completely cover the C-shaped handle or adjusting means 118. The pocket 124 and collar 126 of the shield 122, as they are stretched over the ends of the C-shaped handle 118 and along the support or control shaft of the handle or adjusting means 118, forms a suspended membrane on each side of the handle or adjusting means 118. The rim 128 of the shield 122 creates a snug fit about the support or control shaft of the handle or adjusting means 118 maintaining the shield 122 in position until removal. Thus, the sterile condition of the dental lamp 110 can be maintained by the timely application and removal of the shield 122.

The shield or prophylactic of the present invention, in the case of both embodiments, is recommended to have a thickness in the range of 0.5 to 10 mils. This thickness is desired for the shield to exhibit the desired properties as set forth above. Further, asceptic medicaments and for talc may be applied to the external surface of the shields 22 or 122 to cover application and/or renewal.

The shield or prophylactic 22 of the present invention can be used with all types of dental lamp handles or adjusting means due to its ability to adapt and/or conform to the variety of exterior shapes of the various handles or adjusting means. The present invention provides a significant step forward in reducing the rapid spread of contagious, communicable diseases of the Hepatitus and Acquired Immune Deficiency viral type which are borne on the body fluids and tissues of humans. The shields or prophylactics 22, 122 provide a substantially sterile surface on the exterior of a dental lamp handle or adjusting means which, without the shields, would be a likely place for the harboring and transmittance of the diseases.

The present invention may be embodied in other specific forms without departing from the spirit or essential attributes thereof and, accordingly, reference should be made to the

I claim:

1. A removable disposable sterile dental lamp shield or prophylactic for placement over and in proximate contact with the means for adjusting the illuminated focal point of a dental lamp for significantly reducing the spread of communicable diseases which may be transmitted by or through contact with human body fuilds and tissues during a first and subsequent uses of the dental lamp and its adjusting means in conjunction with the treatment of two or more patients eliminating the need for repeated sterilization of said dental lamp and its adjusting means between such uses for the two or more patients comprising a pocket portion which is substantially cylindrical in shape having closed or sealed ends for fitting over the dental lamp adjusting means and a collar portion which perpendicularly extends outward from a point midway along the cylindrical portion of the shield for maintaining the shield in position on said adjusting means.

2. In acordance with claim 1 wherein said cylindrical and collar portions of the shield have a thickness in the range between 0.5 and 10 mils.

3. In accordance with claim 1 wherein said collar portion has a rim providing a semi-rigid opening for maintaining the sterile integrity of the shield about the opening, said rim having a thickness in the range between 2 and 20 mils.

4. In accordance with claim 1 wherein said aseptic medicaments or talc are applied to the inner surface of the cylindrical and collar portions of the shield for continued disinfection and for lubrication in the application and removal of the shield.

5. In accordance with claim 1 wherein the outer surface of the shield has a medium to high degree of frictional contact.

6. In accordance with claim 1 wherein the shield is made from an elastomeric or elastic material, natural or man-made or any combination therof.

7. In accordance with claim 6 wherein said elastomeric or elastic material exhibits sufficient deformabilty to stretch over the dental lamp adjusting means, toughness and/or tear-resistance to withstand pulling and stretching during application and/or removal and material memory to return to and/or retain its original size and shape after application and/or removal.

8. A removable disposable sterile dental lamp shield or prophylactic for placement over and in proximate contact with the means for adjusting the illuminated focal point of a dental lamp for significantly reducing the spread of communicable diseases which may be transmitted by or through contact with human body fluids and tissues during a first and subsequent uses of the dental lamp and its adjusting means in conjunction with the treatment of two or more patients eliminating the need for repeated sterilization of said dental lamp and its adjusting means between such uses for the two or more patients comprising a pocket portion which is substantially hemispheric in shape having rounded ends and a single aperture or opening for fitting over the dental lamp adjusting means and a collar portion which substantially surrounds said aperture or opening for maintaining the shield in position on said adjusting means.

9. In accordance with claim 8 wherein said cylindrical and collar portions of the shield have a thickness in the range between 0.5 and 10 mils.

10. In accordance with claim 8 wherein said collar portion has a rim providing a semi-rigid opening for maintaining the sterile integrity of the shield about the opening, said rim having a thickness in the range between 2 and 20 mils.

11. In accordance with claim 8 wherein asceptic medicaments or talc are applied to the inner surface of the hemispherical and collar portions of the shield for continued disinfection and for lubrication in the application and removal of the shield.

12. In accordance with claim 8 wherein the outer surface of the shield has a medium to high degree of frictional contact.

13. In accordance with claim 8 wherein the shield is made from an elastomeric or elastic material, natural or man-made or any combination thereof.

14. In accordance with claim 13 wherein said elastomeric or elastic material exhibits sufficient deformability to stretch over the dental lamp adjusting means, toughness and/or tear-resistance to withstand pulling and stretching during application and/or removal and material memory to return to and/or retain its original size and shape after application and/or removal.

* * * * *